United States Patent [19]
Crozier et al.

[11] Patent Number: 5,892,229
[45] Date of Patent: Apr. 6, 1999

[54] METHOD AND APPARATUS FOR MEASURING VAPOROUS HYDROGEN PEROXIDE

[75] Inventors: David Crozier, Indianapolis, Ind.; Gary A. Lang, Canton; Seetha Ananth, Wooster, both of Ohio

[73] Assignee: Rosemount Analytical Inc., La Habra, Calif.

[21] Appl. No.: 635,507

[22] Filed: Apr. 22, 1996

[51] Int. Cl.$^6$ .................................................. G01N 21/35
[52] U.S. Cl. ..................................... 250/339.13; 250/343
[58] Field of Search .............................. 250/343, 339.13, 250/338.5, 339.09, 252.1

[56] References Cited

U.S. PATENT DOCUMENTS

| | | | |
|---|---|---|---|
| 4,182,743 | 1/1980 | Rainer et al. | 422/211 |
| 4,663,961 | 5/1987 | Nelson et al. | . |
| 4,800,279 | 1/1989 | Hieftje et al. | . |
| 5,060,505 | 10/1991 | Tury et al. | 250/339.13 |
| 5,097,130 | 3/1992 | Koashi et al. | 250/343 |
| 5,139,956 | 8/1992 | Schick et al. | 436/52 |
| 5,206,511 | 4/1993 | Apperson et al. | 250/343 |
| 5,334,536 | 8/1994 | Nonnenmacher | 436/135 |
| 5,349,189 | 9/1994 | Maggard | 250/339.07 |
| 5,362,652 | 11/1994 | McClain | 436/135 |
| 5,376,550 | 12/1994 | Fine et al. | 436/47 |
| 5,394,730 | 3/1995 | Crozier et al. | 73/1 G |
| 5,474,938 | 12/1995 | Jadesjö et al. | 436/135 |
| 5,600,142 | 2/1997 | Van Den Berg et al. | . |

FOREIGN PATENT DOCUMENTS

| | | |
|---|---|---|
| 0 285 251 A1 | 10/1988 | European Pat. Off. . |
| 0 418 799 A2 | 3/1991 | European Pat. Off. . |
| 0 744 615 A2 | 11/1996 | European Pat. Off. . |
| 56-2535 | 1/1981 | Japan ................. 250/339.13 |
| 5-281138 | 10/1993 | Japan . |
| 9704816 | 2/1997 | WIPO ................. 250/339.13 |

OTHER PUBLICATIONS

Paul A. Giguere, "The Infra-Red Spectrum of Hydrogen Peroxide", The Journal of Chemical Physics, vol. 18:1, Jan.–Dec., 1950, pp. 88–92.

Davidson et al., "Precision of the Petrochemical Process Analysis Using N/R Spectroscopy", SPIE vol. 1681, Optically Based Methods for Process Analysis, 1992, pp. 231–235.

DiFoggio et al., "Near–infrared offers benefits and challenges in gasoline analysis", Oil & Gas Journal, May 3, 1993, pp. 87–90.

Rosemount Analytical Product Data 103–810, "AOT-F–NIR™ Process Analyzer", Mar., 1995, pp. 1–5.

A. Barbe, M.F. Mérienne, and L.S. Rothman, "On The Potential Of I.R. Limb Emission Spectroscopy for the Measurement Of The Stratospheric Composition", *J. Quant. Spectrosc. Radiat. Transfer,* vol. 52, No. 3/4, 1994, pp. 253–265.

Harris et al, Tunable Diode Laser Measurements of Trace Gases during the 1988 Polarstern Cruise and Intercomparisons with other Methods, *J. Atmos. Chem.,* vol. 15, Nos. 3 and 4, Nov., 1992, pp. 315–326.

Kendall et al., "Detection of Minor Constituents of the Stratosphere by Far Infrared Emission Spectroscopy", *Int. J. Infrared Millimeter Waves,* vol. 2, No. 4, 1981, pp. 783–808.

J. Lodge, Jr., Methods of Air Sampling and Analysis, Third Edition, 1989, pp. 15–17, Lewis Publishers, Inc, Chelsea, Michigan.

*Primary Examiner*—Edward J. Glick
*Attorney, Agent, or Firm*—Westman, Champlin & Kelly, P.A.; S. Koehler

[57] ABSTRACT

The method and apparatus for measuring a content of vaporous hydrogen peroxide in a gaseous medium within an enclosure includes a irradiating a portion of the gaseous medium with light, measuring an absorbance of light in a selected near-infrared wavelength range, and calculating the content of vaporous hydrogen peroxide from the measured absorbance of light.

15 Claims, 8 Drawing Sheets

METHOD AND APPARATUS FOR MEASURING VAPOROUS HYDROGEN PEROXIDE

BACKGROUND OF THE INVENTION

The present invention relates to a method and apparatus for measuring a concentration of vaporous hydrogen peroxide. More particularly, the present invention relates to a method and apparatus that measures the concentration of vaporous hydrogen peroxide continuously in an enclosure.

Hydrogen peroxide has wide commercial use. In the pharmaceutical industry, hydrogen peroxide is commonly used as a sterilant. For instance, hydrogen peroxide is used to sterilize enclosures and equipment of sterile operations. The equipment is located in a sealed enclosure known as an isolation barrier that protects the equipment from contamination. Periodically, the equipment and barrier are shut down for cleaning and sterilization. During sterilization, vaporous hydrogen peroxide is introduced into the barrier. A prior art technique to ensure proper sterilization includes placing biological indicators or challenges within the barrier prior to the sterilization cycle. After the sterilization cycle, which may proceed for one to three hours, the biological challenges are removed from the barrier. The biological challenges are then cultured to promote any growth. Culturing typically takes a minimum of eight hours.

Analysis of the biological challenges determines if any bacteria has survived the sterilization process. If all of the bacteria has been killed, the equipment and the barrier have been properly sterilized. Otherwise, if any bacteria has survived, the sterilization cycle must be repeated.

A significant disadvantage of using biological challenges is the inherent delay necessary to culture the biological challenges after they have been removed from the barrier. The ability of the biological challenges to survive in the presence of vaporous hydrogen peroxide is dependent upon the duration and concentration level of vaporous hydrogen peroxide during the sterilization cycle. If the concentration level of vaporous hydrogen peroxide was sufficiently high for a suitable time period, the biological challenges will not survive and sterilization would be complete.

Although it is well known that vaporous hydrogen peroxide in a sufficient concentration and time duration will kill bacteria and sterilize, a system or method to measure the concentration level of vaporous hydrogen peroxide has not been disclosed.

SUMMARY OF THE INVENTION

A method and apparatus for measuring a content of vaporous hydrogen peroxide in a gaseous medium within an enclosure includes irradiating a portion of the gaseous medium with light, measuring an absorbance of light in a selected near-infrared wavelength range, and calculating the content of vaporous hydrogen peroxide from the measured absorbance of light.

Another aspect of the present invention includes a method and apparatus for generating a known composition of vaporous hydrogen peroxide and water vapor. This aspect of the invention includes injecting a known quantity of aqueous hydrogen peroxide into a known volume of air and vaporizing the known quantity of aqueous hydrogen peroxide.

DETAILED DESCRIPTION OF THE PREFERRED EMBODIMENTS

Figure 1:
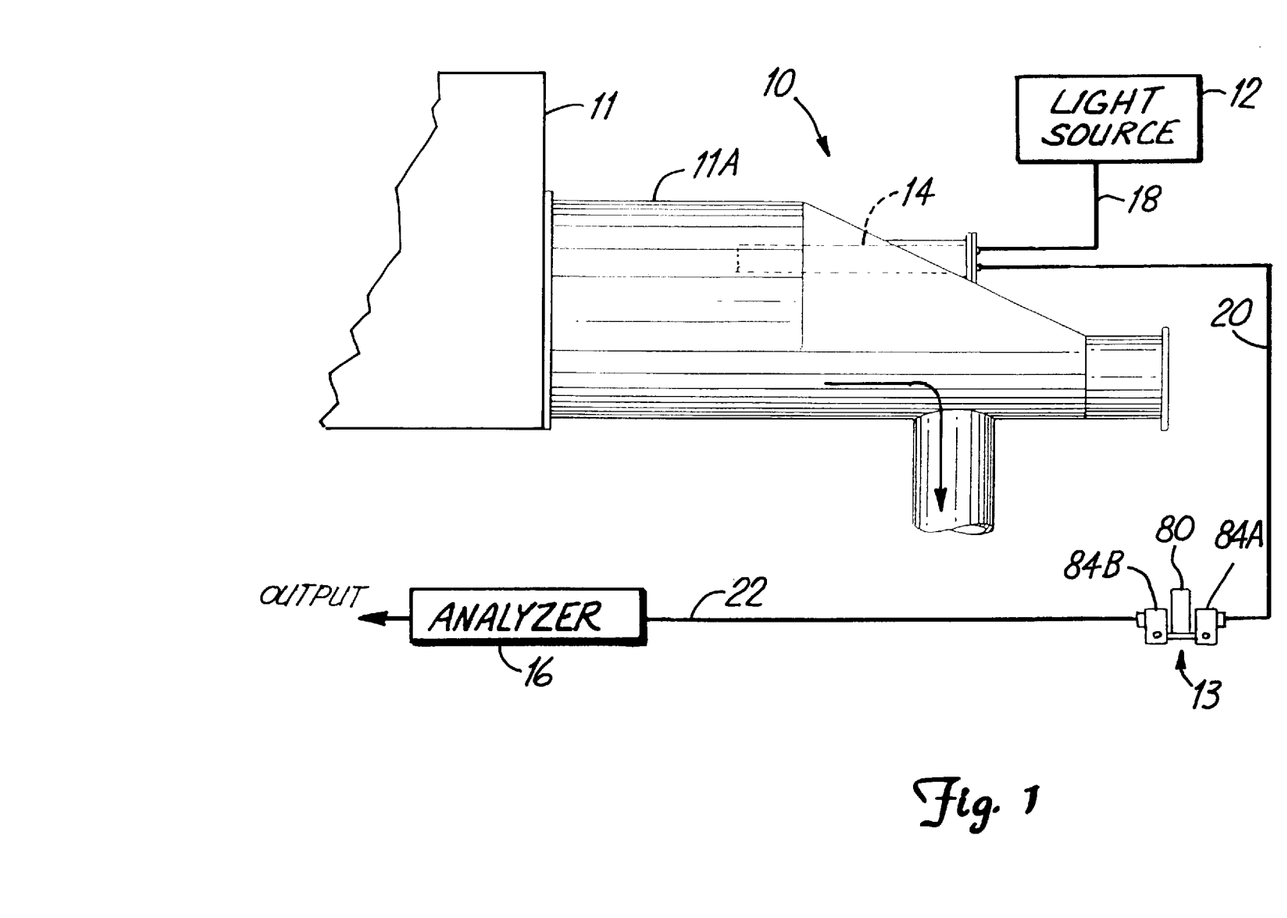
FIG. 1 is diagrammatic view of a system for measuring vaporous hydrogen peroxide in a barrier.

FIG. 1 illustrates a system 10 for measuring vaporous hydrogen peroxide continuously inside a barrier 11. The system 10 includes a light source 12, a sample cell 14 and an analyzer 16. Fiber optic cables indicated at 18, 20 and 22 optically connect the light source 12 to the sample cell 14, and the sample cell 14 to the analyzer 16. In the embodiment illustrated, the system 10 includes a calibration check module 13 optically connected between the sample cell 14 and the analyzer 16. As will be described below, the calibration check module 13 is used periodically to check the operation of the system 10.

Figure 2:
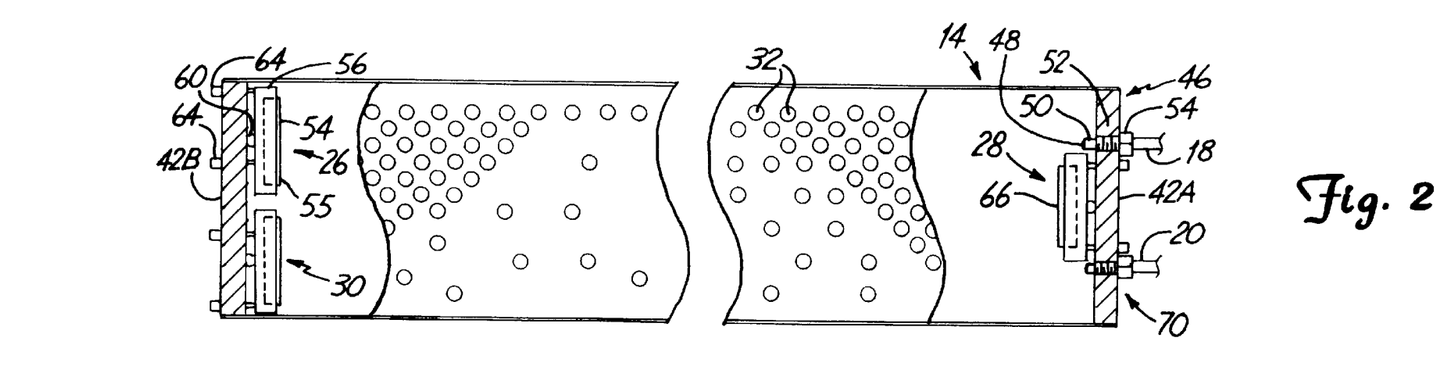
FIG. 2 is side elevational view of a sample cell with portions shown in section.
Figure 3:
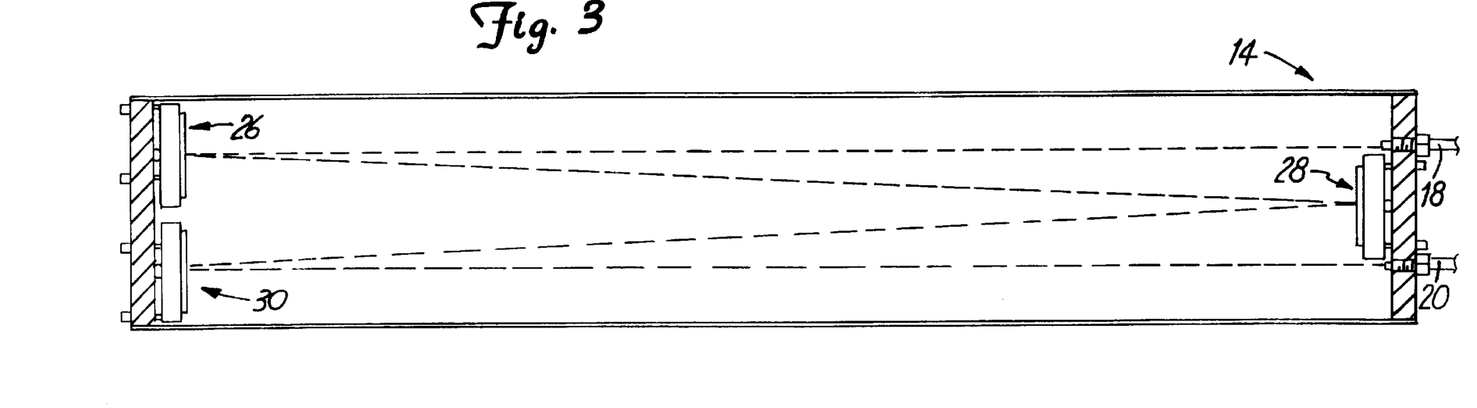
FIG. 3 is a sectional view of the sample cell illustrating light transmitted therein.

Referring also to FIGS. 2 and 3, the light source 12 transmits broad band light through the fiber optic cable 18 and into the sample cell 14. In the embodiment illustrated, the sample cell 14 includes mirror assemblies 26, 28 and 30 that reflect the broad band light in order to increase the distance light travels within the sample cell 14. The sample cell 14 includes a plurality of apertures 32 that allows a gaseous medium within the barrier 11 to enter the sample cell 14. The gaseous medium includes an unknown concentration of vaporous hydrogen peroxide and, typically, an unknown concentration level of water vapor. The vaporous hydrogen peroxide and the water vapor absorb light reflected between the mirror assemblies 26, 28 and 30.

Figure 4:
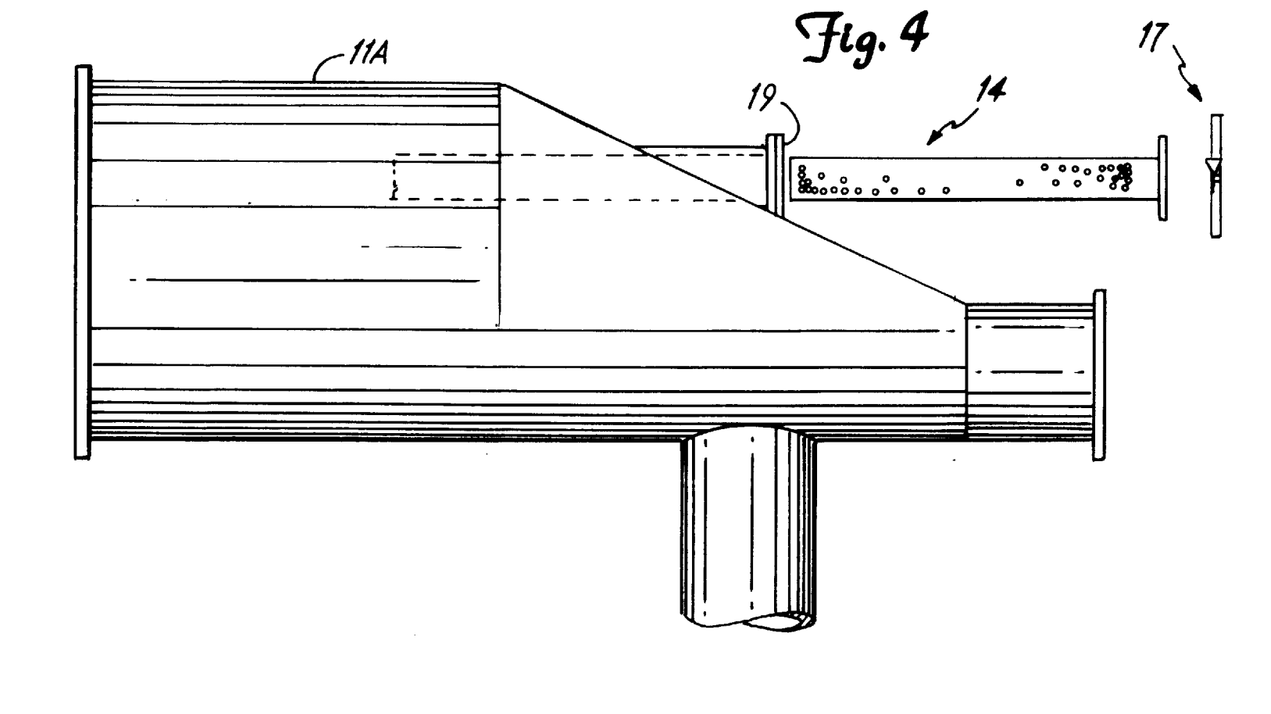
FIG. 4 is an exploded side elevational view of the sample cell and a portion of the barrier.
Figure 5:
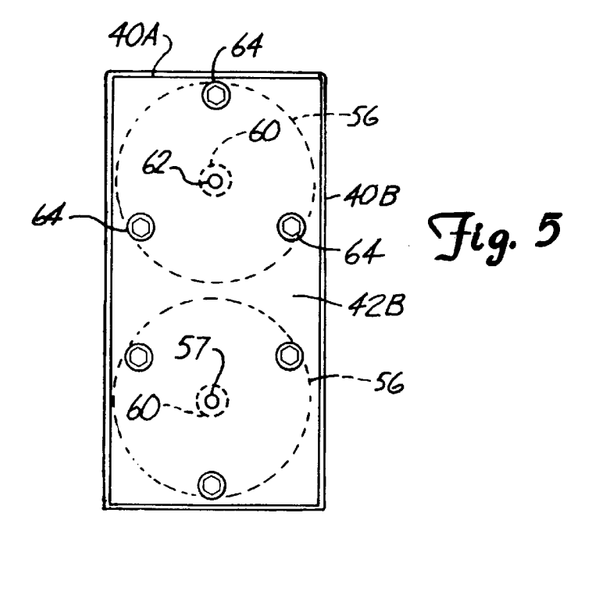
FIG. 5 is a front elevational view of the sample cell.
Figure 6:
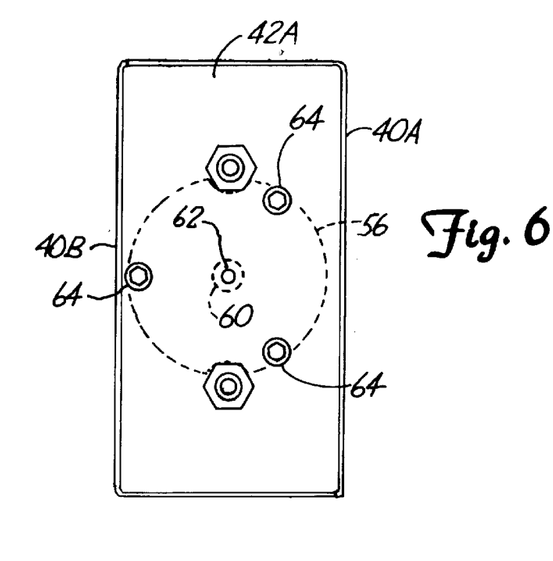
FIG. 6 is a rear elevational view of the sample cell.

The light exits the sample cell 14 through the fiber optic cable 20, and in the embodiment illustrated, is transmitted through the calibration check module 13 and through the fiber optic cable 22 to the analyzer 16. The analyzer 16 measures the light intensity as a function of wavelength over a predetermined wavelength range. By comparing the spectrum obtained in at least one predetermined wavelength range indicative of the absorbance due to vaporous hydrogen peroxide and water vapor with a mathematical calibration model stored within the analyzer 16, the analyzer 16 provides an output signal indicative of the concentration of vaporous hydrogen peroxide, and, if desired, water vapor in the sample cell 14, and thus the barrier 11. In the embodiment illustrated, the sample cell 14 is disposed in a return duct 11A that is used with a hydrogen peroxide generator (not shown) and inlet duct (not shown) to circulate the vaporous hydrogen peroxide throughout the barrier 11 during the sterilization cycle. Referring to FIG. 4, the sample cell 14 is mounted to a sanitary cap 17, which in turn, is secured through an aperture 19 in the return duct 11A using a device known in the industry as a "tri-clamp".

The light source 12 and the analyzer 16 are commercially available and typically sold together. A suitable light source 12 and analyzer 16 are sold by Rosemount Analytical Inc. of Orrville, Ohio, as the AOTF-NIR™ Process Analyzer. The Rosemount Analytical Inc. analyzer includes an acousto-optic tunable filter (a tellurium dioxide ($TeO_2$) crystal with a bonded piezoelectric transducer). The acousto-optic tunable filter combines sound waves and electrical energy to isolate near-infrared light without using moving parts. (In this application, near-infrared, "NIR", refers to light having a wavelength between about 900 nanometers and 2600 nanometers.) Reference is made to U.S. Pat. No. 4,663,961 incorporated herein by reference. Other near-infrared spectrometers, Fourier Transform near-infrared spectrometers, and modified NIR spectrometers of conventional design may be used as the analyzer 16. The preferred mode of operation is transmission, although reflectance and transflectance can also be used.

Referring to FIGS. 2, 3, 5, 6 and 8, the sample cell 14 includes L-shaped wall sections 40A and 40B, which when joined together form a rectangular housing. End caps 42A and 42B are joined to the wall sections 40A and 40B at opposite ends. The end cap 42A supports the mirror assembly 28, while the end cap 42B supports the mirror assemblies 26 and 30. In the embodiment illustrated, a lens assembly 46 supports the fiber optic cable 18 on the sample cell 14 and directs transmitted light from the light source 12 into the sample cell 14. The lens assembly 46 includes a plano convex lens 48. A mount 50 is secured to the end cap 42A and supports the plano convex lens 48. A SMA connector 52 receives the fiber optic cable 18 and is secured into the mount 50. The lens assembly 46 focuses light from the light source 12 on the mirror assembly 26.

Figure 8:
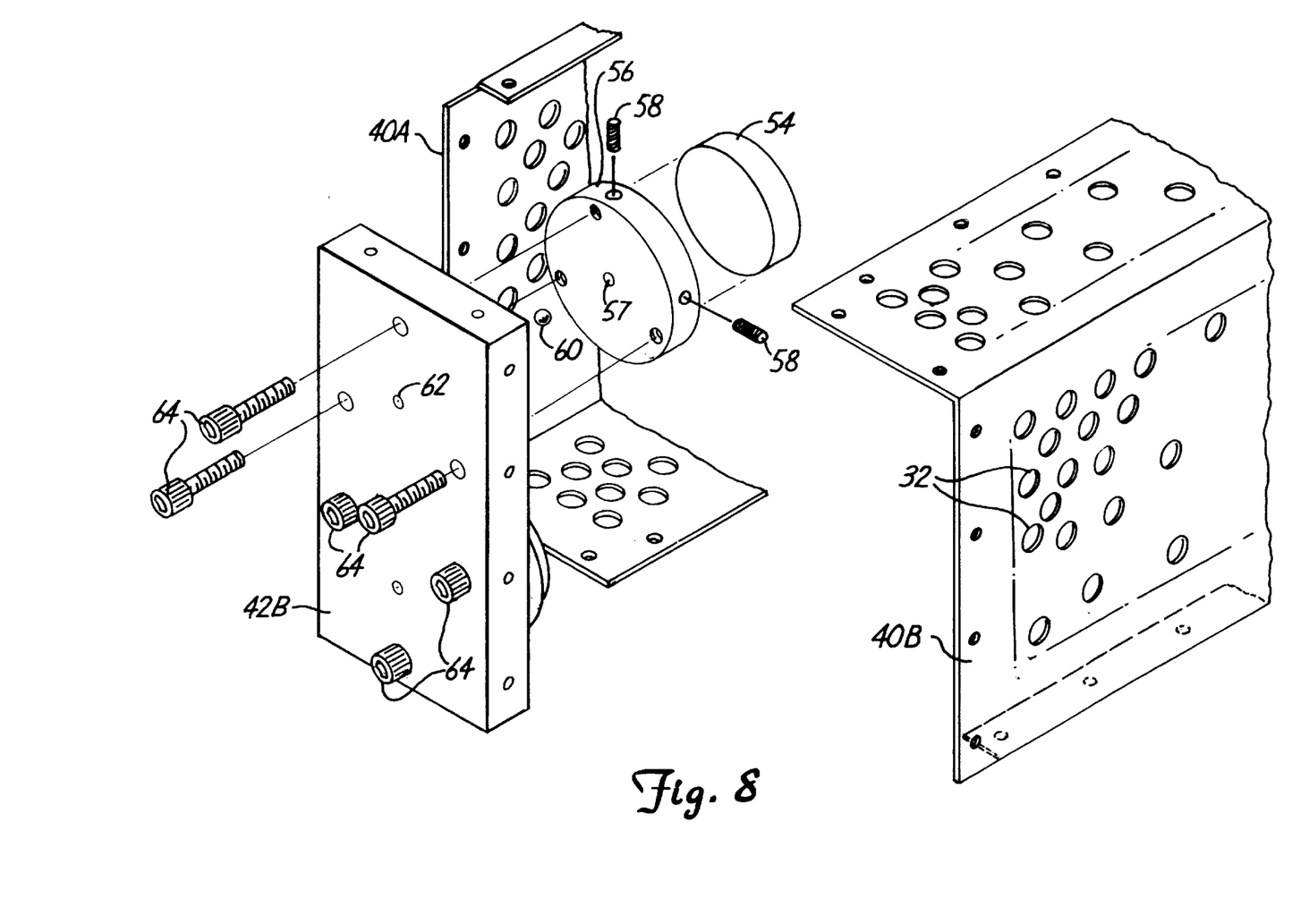
FIG. 8 is an exploded perspective view of a portion of the sample cell.

The mirror assembly 26 receives and reflects light from the lens assembly 46. Referring also to FIG. 8, the mirror assembly 26 includes a spherical concave mirror 54 and a holder 56. A recess 55 (FIG. 2) in the holder 56 receives the spherical concave mirror 54. Setscrews 58 secure the spherical concave mirror 54 to the holder 56. In the embodiment illustrated, the spherical concave mirror 54 is adjustably fixed within the sample cell 14. A pivot ball 60 is interposed between the holder 56 and is seated in an aperture 62 provided in the end cap 42B and a recess 57 in the holder 56. The pivot ball 60 allows pivotal movement of the holder 56 relative to the end cap 42B. Setscrews 64 extend through the end cap 42B and engage the holder 56. By adjusting an exposed length of each of the setscrews 64 from the end cap 42B to the holder 56, the holder 56 and thus the spherical concave mirror 54 can be pivoted on the ball 60.

Light from the spherical concave mirror 54 is received and reflected by the mirror assembly 28. The mirror assembly 28 includes a flat mirror 66. The flat mirror 66 is supported and pivotally adjusted on the end cap 42A in the manner described above with respect to the mirror assembly 26.

Light reflected from the mirror assembly 28 is received and reflected by the mirror assembly 30. The mirror assembly 30 is identical to the mirror assembly 26.

Light reflected from the mirror assembly 30 is received by a lens assembly 70. The lens assembly 70 secures the fiber optic cable 20 to the sample cell 14, and is identical to the lens assembly 46.

The mirror assemblies 26, 28 and 30 increase the path length of the light transmitted between the lens assemblies 46 and 70 without the need for a long sample cell. Trace levels of vaporous hydrogen peroxide can be measured if the path length is approximately 13 feet. For measurement of higher minimum concentration levels, the path length can be shortened.

As illustrated in FIG. 1, the present invention measures the concentration of vaporous hydrogen peroxide within the barrier 11, or "in situ". As used herein "in situ" is defined with respect to the transmitted light in that the light is transmitted through at least a portion of the inside of the barrier 11. Although illustrated using the sample cell 14 being mounted in the barrier 11, it should be understood that the lens assembly 46 and the lens assembly 70 can be mounted directly to walls of the barrier 11 to transmit and receive light through the barrier 11. In situ measurements of vaporous hydrogen peroxide are made in the return duct 11A since typically the lowest concentration of vaporous hydrogen peroxide is in this portion of the barrier 11.

As appreciated by those skilled in the art, the light intensity or absorbance signal from the measurement of vaporous hydrogen peroxide in the sample cell 14 will preferably be mathematically processed to provide an output signal indicative of the concentration in the barrier 11. Preferred techniques for mathematical processing are absorbance base-line offset corrected absorbance data; taking the first, second, third, fourth or higher derivatives of the absorbance spectrum; the technique of dividing the absorbance at one wave length by another; spacial subtraction; and various combinations of these known mathematical techniques. Curve fitting techniques of Savitsky-Golay and Kubelka-Munk, and N-Point Smoothing as well as statistical techniques such as partial least squares and Gauss-Jordan Row reduction can also be used.

Figure 7A:
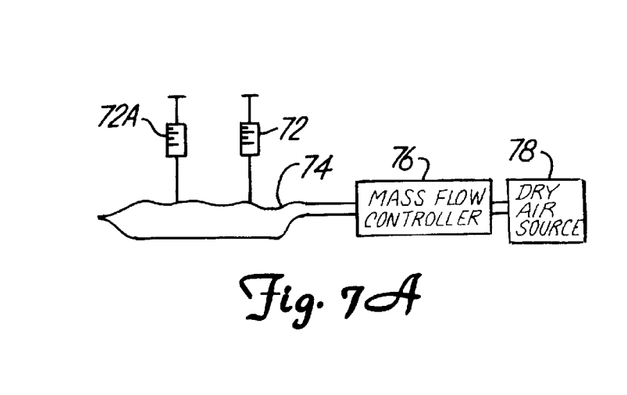
FIG. 7A is a diagrammatic view of an apparatus for preparing a known concentration of vaporous hydrogen peroxide.

Calibration of the analyzer 16 requires obtaining spectra of vaporous hydrogen peroxide at known concentration levels. Another aspect of the present invention includes a unique method of obtaining the required spectra. Referring to FIG. 7A, the method includes vaporizing a known quantity of aqueous hydrogen peroxide and/or water 72 into a suitable enclosure 74 such as a Teflon (polytetrafluorethylene) bag. In the embodiment illustrated, the aqueous hydrogen peroxide and/or water is injected into the bag 74. A mass flow controller 76 allows a known quantity of dry air from a source of dry air 78 to flow into the bag 74. Using the following equations based on the ideal gas law (PV=nRT), a standard reference concentration of vaporous hydrogen peroxide (X) and water vapor (Y) can be calculated:

$$X = \frac{A}{100} \quad 10^3 \frac{(273+T)}{273} \quad \frac{24.414}{34.02} \quad \frac{1.4422}{1} \quad \frac{B}{C} \tag{1}$$

$$Y = \left(1 - \frac{A}{100}\right) 10^3 \frac{(273+T)}{273} \quad \frac{24.414}{18.0} \quad \frac{B}{C} \tag{2}$$

where,

X=ppm of vaporous hydrogen peroxide;

Y=ppm of water vapor;

A=concentration of aqueous hydrogen peroxide in percent;

B=microliters of aqueous hydrogen peroxide;

C=liters of air; and

T=temperature in Celsius of the bag.

Vigorous shaking of the bag 74 and/or heating of the contents of the bag 74 may be required to vaporize completely the aqueous hydrogen peroxide and/or water within the bag 74.

Figure 7B:
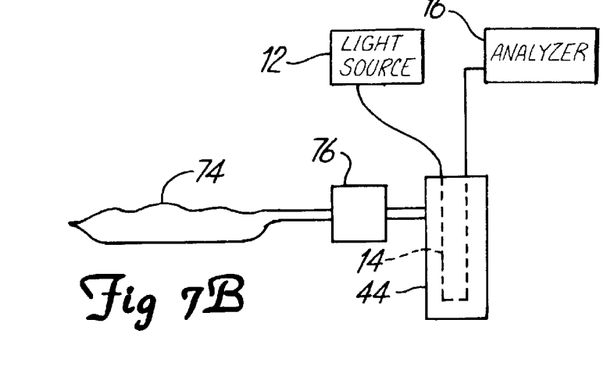
FIG. 7B is a diagrammatic view of supplying the known concentration of vaporous hydrogen peroxide to an enclosure enclosing the sample cell.

A suitable enclosure or calibration standard cell 44 encloses the sample cell 14 and a known quantity of the standard reference concentration is then passed through the calibration standard cell 44, if desired, using the mass flow controller 76. With the light source 12 and the analyzer 16 properly connected to the sample cell 14, a spectrum is obtained for this first concentration level. Additional concentration levels are prepared with the bag 74 and the calibration standard cell 44 evacuated or purged with dry air prior to each subsequent reference concentration. It should be noted that the calibration check module 13 is connected in the light path when reference concentrations are measured if the calibration check module 13 will be present during the measurement of unknown concentrations.

If desired, the concentration level in the bag 74 can be diluted to form additional concentration levels. In this method, the mass flow controller 76 is used to inject a known quantity of dry air into the bag 74. A new lower concentration level of vaporous hydrogen peroxide is obtained. The mass flow controller 76 is then used to provide a known quantity of the new lower reference concentration of hydrogen peroxide to the calibration standard cell 44 in order to obtain a second spectrum. The above steps are repeated to provide other lower reference concentration samples as may be necessary to generate the mathematical model.

In a preferred embodiment, a known quantity of water 72A is injected into the bag 74 and vaporized to a gas phase in addition to the aqueous hydrogen peroxide 72 discussed above. Since a known concentration of aqueous hydrogen peroxide is injected into the bag, a known concentration of vaporous hydrogen peroxide and a known concentration of water vapor in fixed relative proportions are obtained upon vaporization. By injecting additional water vapor into the bag 74, the relative proportions of vaporous hydrogen and water vapor are changed for each reference concentration. Changing the relative proportions of vaporous hydrogen peroxide and water vapor improves the mathematical model.

Figure 9:
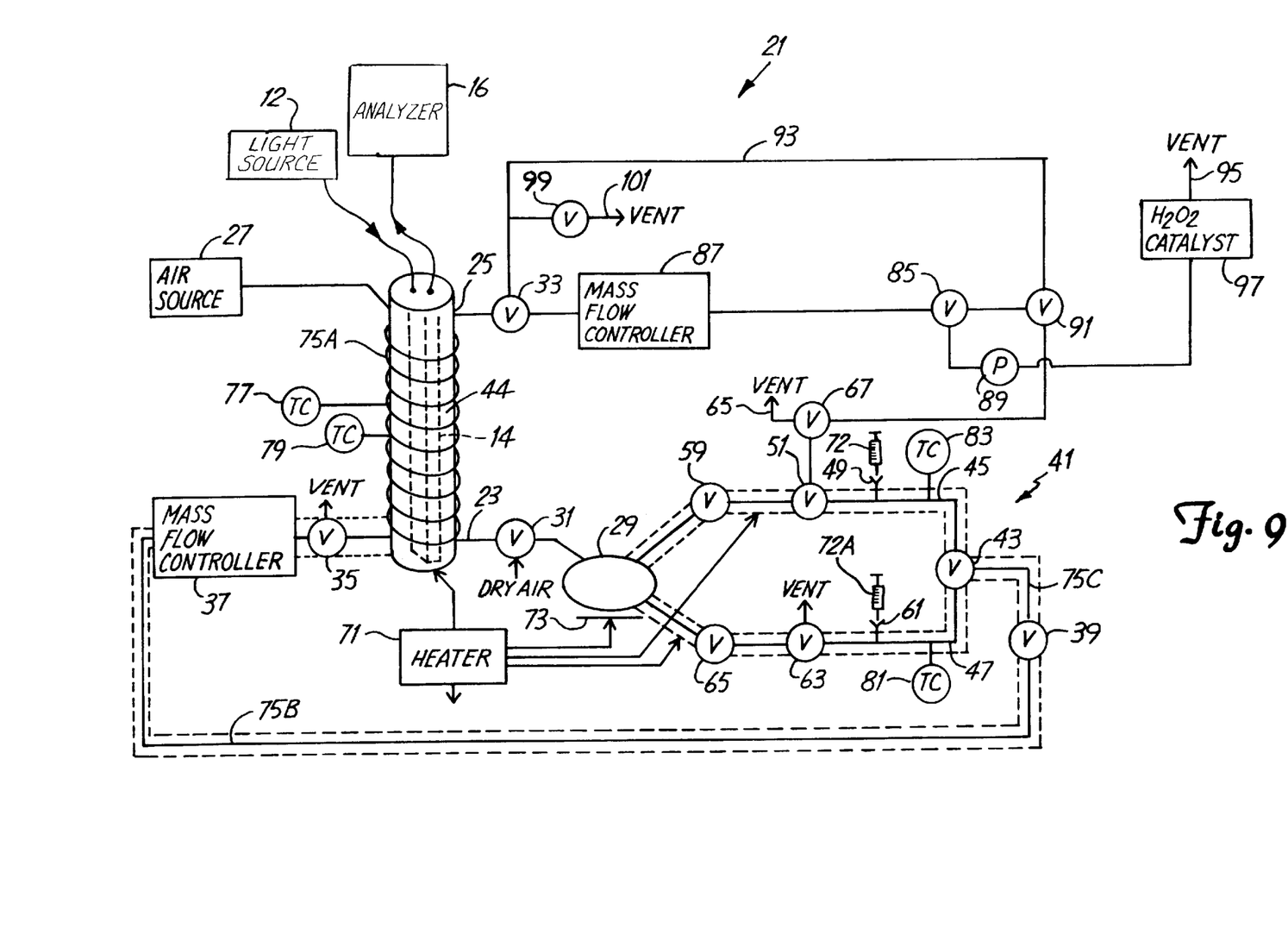
FIG. 9 is a diagrammatic diagram of a system for preparing standard reference concentrations of hydrogen peroxide and water vapor.

A preferred system for generating standard reference concentrations of vaporous hydrogen peroxide and water vapor is illustrated in FIG. 9 at 21. The sample cell 14 is disposed in the calibration standard cell 44. Light generated from the light source 12 is transmitted through the sample cell 14 to the analyzer 16. The calibration standard cell 44 includes an inlet port 23 and an outlet port 25. In general, the system 21 mixes known quantities of vaporous hydrogen peroxide and/or water vapor with air provided from a dry air source 27 in a suitable enclosure 29, such as a Teflon (polytetrafluoroethylene) bag. The standard reference concentrations are provided to the calibration standard cell 44 through a valve 31 fluidly coupled to the inlet port 23. A valve 33 fluidly coupled to the outlet port 25 provides a pathway for the standard reference concentration to exit the calibration standard cell 44 prior to the addition of a new standard reference concentration.

The source of dry air 27 is fluidly coupled to the enclosure 29 through a valve 35, a mass flow controller 37, a valve 39 and an injection apparatus 41. The injection apparatus 41 includes a valve 43 that directs the flow of dry air through a first passageway 45 or a second passageway 47. The first passageway 45 includes an injection port 49 and valves 51 and 59 directing fluid flow into the enclosure 29. The first passageway 45 provides a means for introducing and evaporating (heating) hydrogen peroxide 72 to a gaseous phase. The second passageway 47 is similar to the first passageway 45 and includes an injection port 61 and valves 63 and 65 that direct fluid flow into the enclosure 29. The second passageway 47 provides a means for introducing and evaporating (heating) water 72A to a gaseous phase.

To obtain a known reference concentration in the enclosure 29, dry air is provided through the valve 35, the mass flow controller 37 and the valve 39 to the valve 43. The valve 59 is closed to prevent fluid flow to the enclosure 29, while the valve 51 is operated to fluidly couple the first passageway 45 to a vent 65. In the embodiment illustrated, a valve 67 must be operated to fluidly couple the valve 51 to the vent 65. In this operating state, the injection apparatus 41 couples the source of dry air 27 to the valve 43 in order to substantially fill the first passageway 45 with dry air. Similarly, the second passageway 47 can be filled with dry air by closing valve 65 and operating valves 63 and 43.

With the enclosure 29 previously evacuated and the valves 31 and 65 closed, the valves 51 and 59 are operated to direct air into the enclosure 29. The mass flow controller 37 controls the quantity of dry air entering the enclosure 29 by controlling the rate of flow through the injection apparatus 41. While the dry air flows through the first passageway 45, the known quantity of aqueous hydrogen peroxide 72 is injected into the first passageway 45 through the injection port 49. As the dry air flows through the first passageway 45, the dry air transports the hydrogen peroxide in gaseous form. A sufficient quantity of dry air is swept through the first passageway 45 to ensure that all of the hydrogen peroxide in gaseous form is swept into the enclosure 29.

The second passageway 47 provides a means for injecting additional water 72A and forming a known quantity of water vapor in the enclosure 29. Valve 43 is operated so as to fluidly couple the mass flow controller 37 to the second passageway 47. As dry air flows through the second passageway 47, the known quantity of water 72A is injected through the injection port 61 and transported into the enclosure 29 in gaseous form. Of course, the valve 59 is closed while air flows through the second passageway 47 to isolate the first passageway 45 from the enclosure 29.

In the embodiment illustrated, a heater 71 controls the temperature of the dry air flowing from the air source 27 to the enclosure 29 to ensure injected samples are transported in gaseous form. The heater 71 regulates the temperature of the first passageway 45 so that air flowing through the first passageway 45 does not exceed preferably about 70° C. In this manner, the vaporous hydrogen peroxide does not degrade to water. A temperature of about 70° C. is sufficient to ensure vaporization of hydrogen peroxide from 0 to about 10,000 ppm. Preferably, the temperature is maintained in the range about 50° C. to 70° C. The heater 71 further regulates the temperature of the air flowing through the second passageway 47 so that air flowing through preferably exceeds about 100° C. to ensure proper transfer of the water. In the preferred embodiment, the heater 71 also regulates the temperature of the enclosure 29 (approximately 40° C. but not to exceed about 70° C.) through a heating element 73 placed proximate the enclosure 29, the temperature of the calibration standard cell 44 and the air lines 75A, 75B and 75C extending from the air source 27 to the injection apparatus 41. The air lines 75A, 75B and 75C are heated to preheat the air to a suitable temperature (e.g. 40° C.) prior to entering the injection apparatus 41 to reduce the burden placed upon heating elements heating the first passageway 45 and the second passageway 47. In the embodiment illustrated, the air line 75A is wrapped around the calibration standard cell 44. Thermocouples 77, 79, 81 and 83 are provided to measure the temperature of the air line 75A, the calibration standard cell 44, the second passageway 47 and the first passageway 45, respectively.

With a suitable quantity of the known reference standard in the enclosure 29, the valve 31 is operated so as to fluidly couple the enclosure 29 to the calibration standard cell 44, and the valves 33 and a 85 are operated to fluidly couple a mass flow controller 87 and a pump 89 to the calibration standard cell 44. The pump 89 and the mass flow controller 87 pull a sufficient quantity of the known reference standard from the enclosure 29 through the calibration standard cell 44 to ensure that the calibration standard cell 44 is filled with the known reference standard. The valves 31 and 33 are then operated to seal the calibration standard cell 44. Light transmitted from the light source 12 through the sample cell 14 is received by the analyzer 16 to obtain a spectrum.

After a spectrum has been obtained for the standard reference concentration in the calibration standard cell 44, the calibration standard cell 44 is purged with dry air. In order to quickly purge the calibration standard cell 44, the system 21 includes a line 93 that is fluidly coupled to a valve 91 that in turn is fluidly coupled to the valve 85. The valves 33, 91 and 85 are operated to fluidly couple the outlet port 25 to the pump 89, bypassing the mass flow controller 87. The pump 89 evacuates the calibration standard cell 44, and with the valve 31 open, the enclosure 29 also. The pump 89 pumps the contents of the enclosures 29 and 44 to vent 95 through a decomposition catalyst 97 that reduces the hydrogen peroxide to water and oxygen.

To ensure that all the vaporous hydrogen peroxide and the water vapor has been removed from the calibration standard cell 44, the valve 31 is operated to couple the inlet port 23 to a source of dry air. The valve 33 and a valve 99 are also operated to couple the outlet port 25 to a vent 101. When a sufficient quantity of dry air has been forced through the calibration standard cell 44, the valves 31 and 33 are closed and a spectrum is obtained for the dry air in the calibration standard cell 44, prior to injection of a subsequent standard reference concentration.

Figure 10:
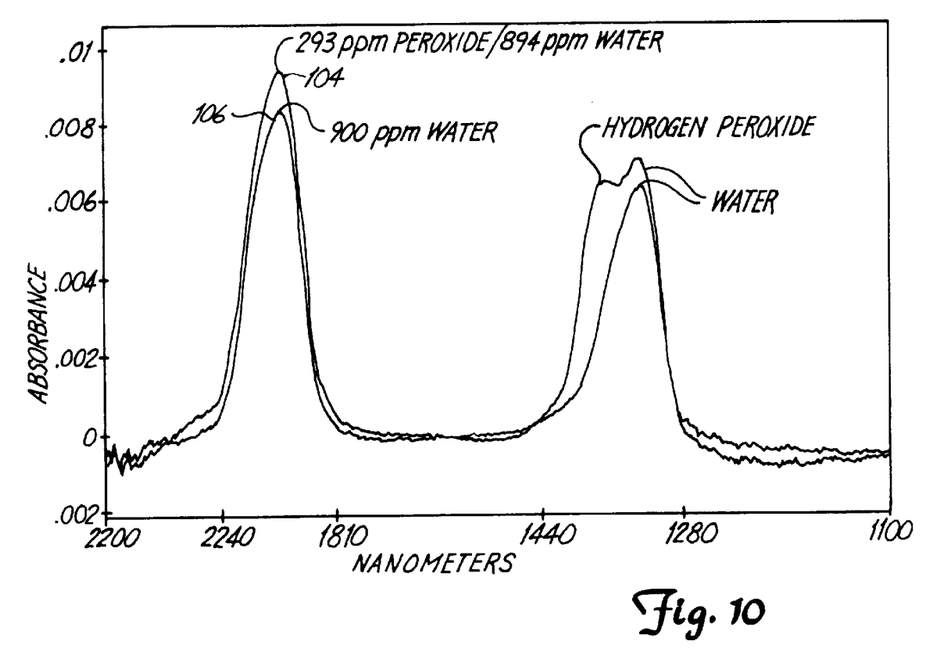
FIG. 10 is a graph of the near-infrared wavelength spectrum for hydrogen peroxide and water vapor.

FIG. 10 illustrates the spectrum for vaporous hydrogen peroxide (293 ppm)/water vapor (894 ppm) 104. Superimposed upon this spectrum is a spectrum of water vapor 106 at a concentration level of 900 ppm to illustrate the contribution of vaporous hydrogen peroxide to a hydrogen peroxide/water vapor mixture 104. It has been found that the spectral absorption characteristics of vaporous and aqueous hydrogen peroxide are sufficiently different that systems for measuring vaporous hydrogen peroxide in the NIR must be specifically tailored to those NIR wavelengths characteristic of vaporous rather than aqueous hydrogen peroxide. Specifically, absorbance in the near-infrared range approximately from 1280–2040 has been found suitable to differentiate vaporous hydrogen peroxide from water vapor and thereby sufficient to calculate the concentration level of vaporous hydrogen peroxide. It has been found that the absorbance of vaporous hydrogen peroxide and water vapor in the wavelength range approximately from 1280–1440 nanometers is particularly useful for determining vaporous hydrogen peroxide and water vapor simultaneously since it is possible to identify characteristic wavelengths for each component. Absorbances for vaporous hydrogen peroxide and water vapor in the wavelength range approximately 1810–2040 nanometers can be used separately or together with the first-mentioned wavelength range to also identify characteristic wavelengths for vaporous hydrogen peroxide and water vapor.

Figure 11:
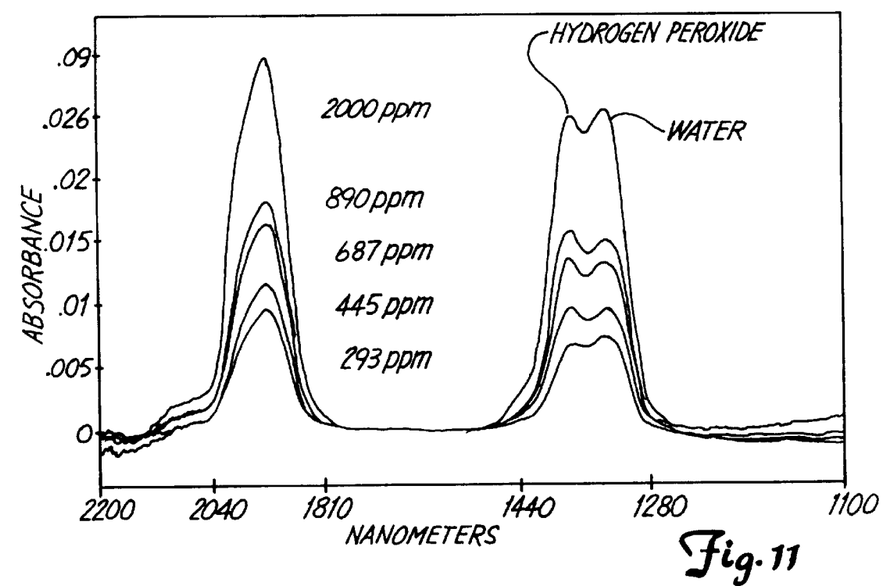
FIG. 11 is a graph of the near-infrared wavelength spectrum for a plurality of hydrogen peroxide and water vapor mixtures.

FIG. 11 illustrates spectra for a plurality of mixtures of hydrogen peroxide/water vapor having gaseous hydrogen peroxide concentration levels of 293 ppm, 445 ppm, 687 ppm, 890 ppm and 2000 ppm. The analyzer 16, using statistical modeling techniques described above, generates mathematical equations that can be used to analyze unknown test samples.

It is desirable to check the calibration of the model periodically to confirm optical performance. Although one could use known reference concentrations to check the calibration of the system 10, this technique requires the operator to prepare or obtain reference standards. As illustrated in FIG. 1, the calibration check module 13 is coupled in series with the in-situ sample cell 14 to confirm optical performance.

Figure 12:
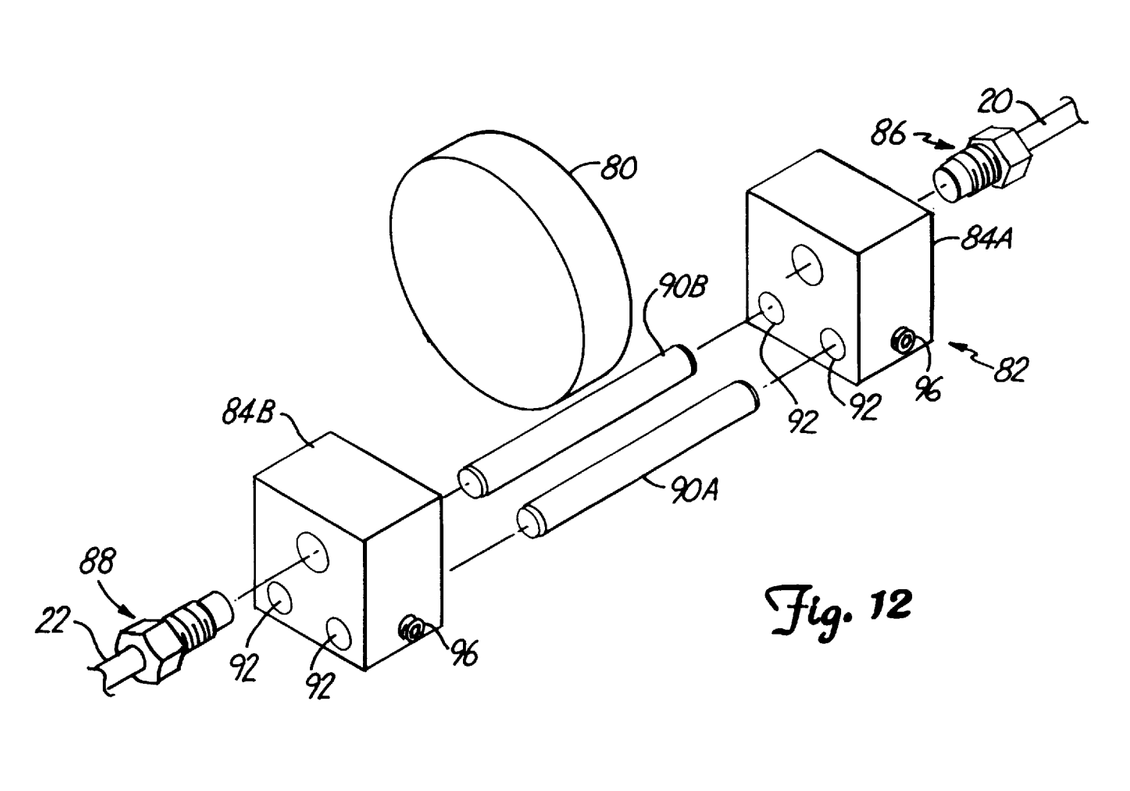
FIG. 12 is an exploded perspective view of a calibration check module.

The calibration check module 13 is illustrated in detail in FIG. 12. The calibration check module 13 includes a neutral density filter 80 and a support structure 82 that supports the neutral density filter 80 in the light path from the light source 12 to the analyzer 16. Suitable neutral density filters are available from suppliers, such as, CVI Laser Corporation of Albuquerque, N. Mex. The neutral density filter 80 is periodically disposed in the light path and attenuates the light transmitted by a constant amount across the near-infrared wavelength range. In the embodiment illustrated, the calibration check module 13 couples light from the sample cell 14 to the analyzer 16, if desired, the calibration check module 13 can be coupled between the light source 12 and the sample cell 14.

The support structure 82 includes end blocks 84A and 84B. A lens assembly 86, substantially identical to the lens assembly 46 discussed above, joins the fiber optic cable 20 to the end block 84A. A lens assembly 88, also substantially identical to the lens assembly 46 described above, couples the fiber optic cable 22 to the end block 84B. Guide rods 90A and 90B extend between the end blocks 84A and 84B to support the neutral density filter 80 between the end blocks 84A and 84B. The guide rods 90A and 90B are received in corresponding apertures 92 provided in each of the end blocks 84A and 84B. The end blocks 84A and 84B slide on the guide rods 90A and 90B toward and away from each other. In this manner, the distance between opposed surfaces of the end blocks 84A and 84B can be adjusted to accommodate the thickness of the neutral density filter 80. Setscrews, two of which are illustrated at 96, are received in corresponding threaded apertures in the end blocks 84A and 84B to engage the guide rods 90A and 90B and secure the end blocks 84A and 84B in position.

Although the present invention has been described with reference to preferred embodiments, workers skilled in the art will recognize that changes may be made in form and detail without departing from the spirit and scope of the invention.

What is claimed is:

1. A method of measuring a content of vaporous hydrogen peroxide in a gaseous medium within an enclosure, wherein the gaseous medium includes water vapor, the method comprising the steps of:

irradiating a portion of the gaseous medium with light;

measuring an absorbance of light in a selected near-infrared wavelength range; and calculating the content of vaporous hydrogen peroxide in the presence of the water vapor from the measured absorbance of light.

2. The method of claim 1 wherein the selected near-infrared wavelength range comprises 1280–2040 nanometers.

3. The method of claim 2 wherein the selected near-infrared wavelength range comprises 1280–1440 nanometers.

4. The method of claim 2 wherein the selected near-infrared wavelength range comprises 1810–2040 nanometers.

5. The method of claim 1 wherein the enclosure includes an inlet for receiving vaporous hydrogen peroxide from a vaporous hydrogen peroxide generator and a return duct for returning vaporous hydrogen peroxide and water vapor thereto, and wherein the step of measuring includes measuring the absorbance of light of the gaseous medium in the return duct.

6. The method of claim 1 and further comprising the steps of:

provinding a system comprising a light source, an analyzer and a light transmission path from the light source to the analyzer through a sample location whereat the portion of gaseous medium is disposed; and attenuating the light in the light transmission path other than with the portion of the gaseous medium to confirm operation of the system.

7. The method of claim 6 wherein the step of attenuating the light includes positioning a light attenuator in the light transmission path remote from the sample location.

8. The method of claim 7 wherein the light attenuator comprises a removable filter.

9. A system for measuring a content of vaporous hydrogen peroxide in a gaseous medium in an enclosure, wherein the gaseous medium includes water vapor, the system comprising:

a light source coupled to the enclosure to irradiate a portion of the gaseous medium;

a light receiver coupled to the enclosure to receive light from said light source, the light receiver providing a light output signal indicative of light absorbance in a selected near-infrared wavelength range; and an analyzer receiving the light output signal and calculating the content of vaporous hydrogen peroxide in the enclosure in the presence of water vapor.

10. The system of claim 9 wherein the selected near-infrared wavelength range comprises 1280–2040 nanometers.

11. The system of claim 10 wherein the selected near-infrared wavelength range comprises 1280–1440 nanometers.

12. The system of claim 10 wherein the selected near-infrared wavelength range comprises 1810–2040 nanometers.

13. The system of claim 9 further comprising a first fiber optic cable coupling the light source to the enclosure and a second fiber optic cable coupling the light receiver to the analyzer and transmitting the light output signal.

14. The system of claim 9 wherein the light source and the analyzer are disposed outside of the enclosure.

15. The system of claim 9 wherein the enclosure includes an inlet for receiving vaporous hydrogen peroxide from a vaporous hydrogen peroxide generator and a return duct for returning vaporous hydrogen peroxide and water vapor thereto, and wherein the light receiver is disposed in the return duct.

* * * * *

UNITED STATES PATENT AND TRADEMARK OFFICE
CERTIFICATE OF CORRECTION

PATENT NO. : 5,892,229
DATED : April 6, 1999
INVENTOR(S) : David Crozier, et al.

It is certified that error appears in the above-identified patent and that said Letters Patent is hereby corrected as shown below:

Add the following claims: Column 10, line 30, insert

--16. The system of claim 9 and further comprising:
  a light transmission path transmitting light from the light source to the analyzer through the gaseous medium;
  a light attenuator other than the gaseous medium selectively positioned in the light transmission path; and
    wherein the analyzer detects the presence of the light attenuator.--

--17. The system of claim 16 wherein the light attenuator comprises a removable filter attenuating light in a selected range of wavelengths.--

Signed and Sealed this

Thirteenth Day of July, 1999

*Attest:*

Q. TODD DICKINSON

*Attesting Officer*  Acting Commissioner of Patents and Trademarks